US00RE49680E

(19) United States
(12) Reissued Patent
Stokely et al.

(10) Patent Number: US RE49,680 E
(45) Date of Reissued Patent: Oct. 3, 2023

(54) SYSTEMS AND METHODS FOR SPREAD SPECTRUM DISTRIBUTED ACOUSTIC SENSOR MONITORING

(71) Applicant: Adelos, Inc., Polson, MT (US)

(72) Inventors: Christopher Stokely, Houston, TX (US); Neal G. Skinner, Lewisville, TX (US); Leonardo De Oliveira Nunes, Rio de Janeiro (BR)

(73) Assignee: ADELOS, LLC, San Diego, CA (US)

(21) Appl. No.: 16/542,187

(22) Filed: Aug. 15, 2019

Related U.S. Patent Documents

Reissue of:

(64) Patent No.: 9,733,120
Issued: Aug. 15, 2017
Appl. No.: 14/903,503
PCT Filed: Aug. 12, 2013
PCT No.: PCT/US2013/054588
§ 371 (c)(1),
(2) Date: Jan. 7, 2016
PCT Pub. No.: WO2015/023255
PCT Pub. Date: Feb. 19, 2015

(51) Int. Cl.
*G01H 9/00* (2006.01)
*G01H 3/00* (2006.01)

(52) U.S. Cl.
CPC ..... *G01H 9/004* (2013.01); *G01H 3/00* (2013.01)

(58) Field of Classification Search
CPC ..... G01H 9/004; G01H 3/00; G01N 29/14
See application file for complete search history.

(56) References Cited

U.S. PATENT DOCUMENTS

| | | | |
|---|---|---|---|
| 4,238,856 | A | 12/1980 | Bucaro et al. |
| 4,775,216 | A | 10/1988 | Layton |
| 4,817,101 | A | 3/1989 | Wyeth et al. |
| 4,889,986 | A | 12/1989 | Kersey et al. |
| 4,898,443 | A | 2/1990 | Epworth et al. |
| 4,968,880 | A | 11/1990 | Beller |
| 5,000,568 | A | 3/1991 | Trutna et al. |
| 5,115,332 | A | 5/1992 | Naito et al. |
| 5,146,359 | A | 9/1992 | Okoshi et al. |
| 5,177,764 | A | 1/1993 | Nilsson |
| 5,194,847 | A | 3/1993 | Taylor et al. |
| 5,212,825 | A | 5/1993 | Layton |
| 5,353,627 | A | 10/1994 | Diatschenko et al. |
| 5,371,588 | A | 12/1994 | Davis et al. |
| 5,633,741 | A | 5/1997 | Giles |

(Continued)

FOREIGN PATENT DOCUMENTS

| | | |
|---|---|---|
| CN | 100346669 | 10/2007 |
| CN | 201829006 U | 5/2011 |

(Continued)

OTHER PUBLICATIONS

"Fiber Couplers", RP Photonics Encyclopedia, pp. 1-3, www.rp-photonics.com/fiber_couplers.html.

(Continued)

*Primary Examiner* — Cameron Saadat
(74) *Attorney, Agent, or Firm* — Volpe Koenig

(57) ABSTRACT

A method and device for monitoring oil field operations with a fiber optic distributed acoustic sensor (DAS) that uses a continuous wave laser light source and modulates the continuous wave output of the laser light source with pseudo-random binary sequence codes.

27 Claims, 7 Drawing Sheets

(56) References Cited

U.S. PATENT DOCUMENTS

| | | | | |
|---|---|---|---|---|
| 5,635,829 | A | 6/1997 | Hamada | |
| 5,686,986 | A | 11/1997 | Li et al. | |
| 5,694,408 | A | 12/1997 | Bott et al. | |
| 5,696,863 | A * | 12/1997 | Kleinerman | G01D 5/3538 250/227.11 |
| 5,754,293 | A | 5/1998 | Farhadiroushan | |
| 5,844,235 | A | 12/1998 | Tachikawa et al. | |
| 5,847,816 | A | 12/1998 | Zediker et al. | |
| 5,847,817 | A | 12/1998 | Zediker et al. | |
| 5,946,131 | A | 8/1999 | Wells et al. | |
| 5,956,355 | A | 9/1999 | Swanson et al. | |
| 5,991,479 | A * | 11/1999 | Kleinerman | G01J 5/08 250/227.11 |
| 6,008,487 | A | 12/1999 | Tachikawa et al. | |
| 6,034,760 | A | 3/2000 | Rees | |
| 6,043,921 | A | 3/2000 | Payton | |
| 6,111,816 | A | 8/2000 | Chiang et al. | |
| 6,127,948 | A | 10/2000 | Hillis et al. | |
| 6,173,091 | B1 | 1/2001 | Reich | |
| 6,216,540 | B1 | 4/2001 | Nelson et al. | |
| 6,236,652 | B1 | 5/2001 | Preston et al. | |
| 6,285,806 | B1 | 9/2001 | Kersey et al. | |
| 6,571,034 | B2 | 5/2003 | Bhagavatula | |
| 6,597,821 | B1 | 7/2003 | Bohnert et al. | |
| 6,626,043 | B1 | 9/2003 | Bailey et al. | |
| 6,630,658 | B1 | 10/2003 | Bohnert et al. | |
| 6,700,655 | B2 | 3/2004 | Uchiyama et al. | |
| 7,030,971 | B1 | 4/2006 | Payton | |
| 7,142,736 | B2 | 11/2006 | Patel et al. | |
| 7,268,863 | B2 | 9/2007 | Payton | |
| 7,271,884 | B2 | 9/2007 | Payton | |
| 7,274,441 | B2 | 9/2007 | Payton | |
| 7,339,721 | B1 | 3/2008 | Berkey et al. | |
| 7,355,163 | B2 | 4/2008 | Watley et al. | |
| 7,565,334 | B2 | 7/2009 | Rifkin et al. | |
| 7,646,944 | B2 | 1/2010 | Kaplan | |
| 7,946,341 | B2 | 5/2011 | Hartog et al. | |
| 8,045,143 | B2 | 10/2011 | Harres | |
| 8,408,064 | B2 | 4/2013 | Hartog et al. | |
| 8,417,490 | B1 | 4/2013 | Preston et al. | |
| 8,514,381 | B2 | 8/2013 | Shao et al. | |
| 8,587,479 | B2 | 11/2013 | Kurokawa | |
| 9,008,506 | B2 | 4/2015 | Hsiao et al. | |
| 9,733,120 | B2 | 8/2017 | Stokely et al. | |
| 9,766,141 | B2 | 9/2017 | Preston et al. | |
| 9,772,238 | B2 | 9/2017 | Preston et al. | |
| 10,203,264 | B2 | 2/2019 | Preston et al. | |
| 2001/0050768 | A1 | 12/2001 | Uchiyama et al. | |
| 2002/0154291 | A1 | 10/2002 | Uchiyama et al. | |
| 2004/0114939 | A1 | 6/2004 | Taylor | |
| 2005/0077455 | A1 | 4/2005 | Townley-Smith et al. | |
| 2005/0149264 | A1 | 7/2005 | Tarvin et al. | |
| 2005/0174563 | A1 | 8/2005 | Evans et al. | |
| 2005/0254038 | A1 | 11/2005 | Harres | |
| 2006/0018586 | A1 | 1/2006 | Kishida | |
| 2006/0028636 | A1 | 2/2006 | Payton | |
| 2006/0066839 | A1 | 3/2006 | Payton | |
| 2006/0126991 | A1 | 6/2006 | Huang | |
| 2006/0227315 | A1 | 10/2006 | Beller | |
| 2006/0232765 | A1 | 10/2006 | Harres | |
| 2007/0018635 | A1 | 1/2007 | Nebendahl | |
| 2007/0113649 | A1 | 5/2007 | Bharti et al. | |
| 2007/0171400 | A1 | 7/2007 | Payton | |
| 2007/0194796 | A1 | 8/2007 | Harrison et al. | |
| 2008/0036597 | A1 | 2/2008 | Harman | |
| 2008/0145049 | A1 | 6/2008 | Koyamada | |
| 2009/0006840 | A1 | 1/2009 | Birger et al. | |
| 2009/0173494 | A1 | 7/2009 | Tarvin et al. | |
| 2009/0222541 | A1 | 9/2009 | Monga et al. | |
| 2009/0252491 | A1 * | 10/2009 | Healey | H04B 10/00 398/16 |
| 2010/0002226 | A1 | 1/2010 | Hartog | |
| 2010/0098438 | A1 | 4/2010 | Prat Goma et al. | |
| 2010/0238429 | A1 | 9/2010 | Hayward et al. | |
| 2010/0284021 | A1 | 11/2010 | Hacker | |
| 2010/0290035 | A1 | 11/2010 | Wang et al. | |
| 2011/0228255 | A1 * | 9/2011 | Li | G01B 11/18 356/33 |
| 2012/0067118 | A1 | 3/2012 | Hartog et al. | |
| 2013/0229649 | A1 | 9/2013 | Li et al. | |
| 2014/0130601 | A1 | 5/2014 | Zhou et al. | |
| 2014/0208855 | A1 | 7/2014 | Skinner | |
| 2014/0255023 | A1 | 9/2014 | Kishida et al. | |
| 2014/0268110 | A1 | 9/2014 | Hartog | |
| 2015/0211983 | A1 * | 7/2015 | Speck | G01N 21/1702 73/152.18 |
| 2016/0124407 | A1 | 5/2016 | Kallio et al. | |
| 2016/0187223 | A1 | 6/2016 | Preston et al. | |
| 2016/0252414 | A1 | 9/2016 | Preston et al. | |
| 2016/0320232 | A1 * | 11/2016 | Nunes | G01M 3/24 |
| 2017/0284895 | A9 | 10/2017 | Preston et al. | |
| 2019/0219478 | A1 | 7/2019 | Preston et al. | |

FOREIGN PATENT DOCUMENTS

| | | | |
|---|---|---|---|
| EP | 2950069 | A1 | 12/2015 |
| GB | 2190186 | A | 11/1987 |
| GB | 2372100 | A | 8/2002 |
| JP | 2013079906 | A | 5/2013 |
| JP | 2013181789 | A | 9/2013 |
| KR | 1020130081062 | A | 7/2013 |
| WO | 8707014 | A2 | 11/1987 |
| WO | 9746870 | A1 | 12/1997 |
| WO | 0068645 | A1 | 11/2000 |
| WO | 2004034096 | A2 | 4/2004 |
| WO | 2006017702 | A2 | 2/2006 |
| WO | 2016033192 | A1 | 3/2016 |
| WO | 2016033199 | A1 | 3/2016 |

OTHER PUBLICATIONS

Choi et al., "Distributed fiber-optic pressure/seismic sensor for low-cost monitoring of long perimeters", Unattended Ground Sensor Technologies and Applications V, 2003, pp. 134-141, vol. 5090, Proceedings of SPIE.

European Patent Office, "Communication pursuant to Article 94(3) from EP Application No. 05782661.2", from Foreign Counterpart to U.S. Appl. No. 11/056,630, dated Apr. 29, 2013, pp. 1-7, Published: EP.

European Patent Office, "Communication pursuant to Article 94(3) from EP Application No. 15177492.4", from Foreign Counterpart to U.S. Appl. No. 11/056,630, dated Dec. 21, 2018, pp. 1-7, Published: EP.

European Patent Office, "Extended European Search Report from EP Application No. 05782661.2", from Foreign Counterpart to U.S. Appl. No. 11/056,630, dated Feb. 7, 2011, pp. 1-48, Published: EP.

European Patent Office, "Extended European Search Report from EP Application No. 15177492.4", from Foreign Counterpart to U.S. Appl. No. 11/056,630, dated Oct. 7, 2015, pp. 1-7, Published: EP.

Hughes et al., "Static pressure sensitivity amplification in interferometric fiber-optic hydrophones", Applied Optics, Jan. 1, 1980, pp. 98-107, vol. 19, No. 1.

International Bureau, "International Preliminary Report on Patentability from PCT Application No. PCT/US2005/027821", from Foreign Counterpart to U.S. Appl. No. 11/056,630, dated Feb. 6, 2007, pp. 1-4, Published WO.

International Bureau, "International Preliminary Report on Patentability from PCT Application No. PCT/US2015/046966", from Foreign Counterpart to U.S. Appl. No. 14/837,592, dated Mar. 9, 2017, pp. 1-9, Published: WO.

International Bureau, "International Preliminary Report on Patentability from PCT Application No. PCT/US2015/046973", from Foreign Counterpart to U.S. Appl. No. 14/837,609, dated Mar. 9, 2017, pp. 1-7, Published: WO.

International Searching Authority, "International Search Report and Written Opinion from PCT Application No. PCT/US15/46973", from Foreign Counterpart to U.S. Appl. No. 14/837,609, dated Nov. 30, 2015, pp. 1-8, Published: WO.

(56) References Cited

OTHER PUBLICATIONS

International Searching Authority, "International Search Report and Written Opinion from PCT Application No. PCT/US2015/046966", from Foreign Counterpart to U.S. Appl. No. 14/837,592, dated Nov. 23, 2015, pp. 1-10, Published: WO.
International Searching Authority, "Written Opinion of the International Searching Authority from PCT Application No. PCT/US05/27821", from Foreign Counterpart to U.S. Appl. No. 11/056,630, dated Feb. 17, 2006, pp. 1-3, Published: WO.
Ishida et al., "Lightwave Scalar Network Analyser Employing Optical Heterodyne Detection", Electronics Letters, Mar. 1, 1990, pp. 297-298, vol. 26, No. 5, Electronics Letters.
Liokumovich et al., "Fundamentals of optical fiber sensing schemes based on coherent optical time domain reflectometry: Signal model under static fiber conditions", Journal of Lightwave Technology, 2015, pp. 1-11, IEEE.
Maughan et al., "Novel distributed fibre sensor using microwave heterodyne detection of spontaneous Brillouin backscatter", Fourteenth International Conference on Optical Fiber Sensors, 2000, pp. 1-5, vol. 4185, SPIE.
Park et al., "Fiber Optics Intrusion Sensor using Coherent Optical Time Domain Reflectometer", Japanese Journal of Applied Physics, Jun. 2003, pp. 2481-2482, vol. 42, The Japan Society of Applied Physics.
U.S. Patent and Trademark Office, "Advisory Action", U.S. Appl. No. 14/837,592, dated Jan. 22, 2018, pp. 1-3, Published: US.
U.S. Patent and Trademark Office, "Decision on Petition", U.S. Appl. No. 14/837,592, dated Jun. 28, 2017, pp. 1-4, Published: US.
U.S. Patent and Trademark Office, "Decision on Petition", U.S. Appl. No. 14/837,609, dated Sep. 1, 2017, pp. 1-3, Published: US.
U.S. Patent and Trademark Office, "Final Office Action", U.S. Appl. No. 14/837,592, dated Nov. 8, 2017, pp. 1-21, Published: US.
U.S. Patent and Trademark Office, "Office Action", U.S. Appl. No. 14/190,478, dated Jun. 26, 2019, pp. 1-169, Published: US.
U.S. Patent and Trademark Office, "Office Action", U.S. Appl. No. 14/837,592, dated Mar. 12, 2018, pp. 1-15, Published: US.
U.S. Patent and Trademark Office, "Office Action", U.S. Appl. No. 14/837,592, dated May 11, 2017, pp. 1-31, Published: US.
U.S. Patent and Trademark Office, "Office Action", U.S. Appl. No. 15/154,161, dated Sep. 23, 2016, pp. 1-13, Published: US.
U.S. Patent and Trademark Office, "Office Action", U.S. Appl. No. 14/686,161, dated Oct. 18, 2016, pp. 1-134, Published: US.
European Patent Office, "Extended European Search Report from EP Application No. 05782661.2", from Foreign Counterpart to U.S. Appl. No. 11/056,630, dated Feb. 7, 2011, pp. 1-15, Published: EP.

* cited by examiner

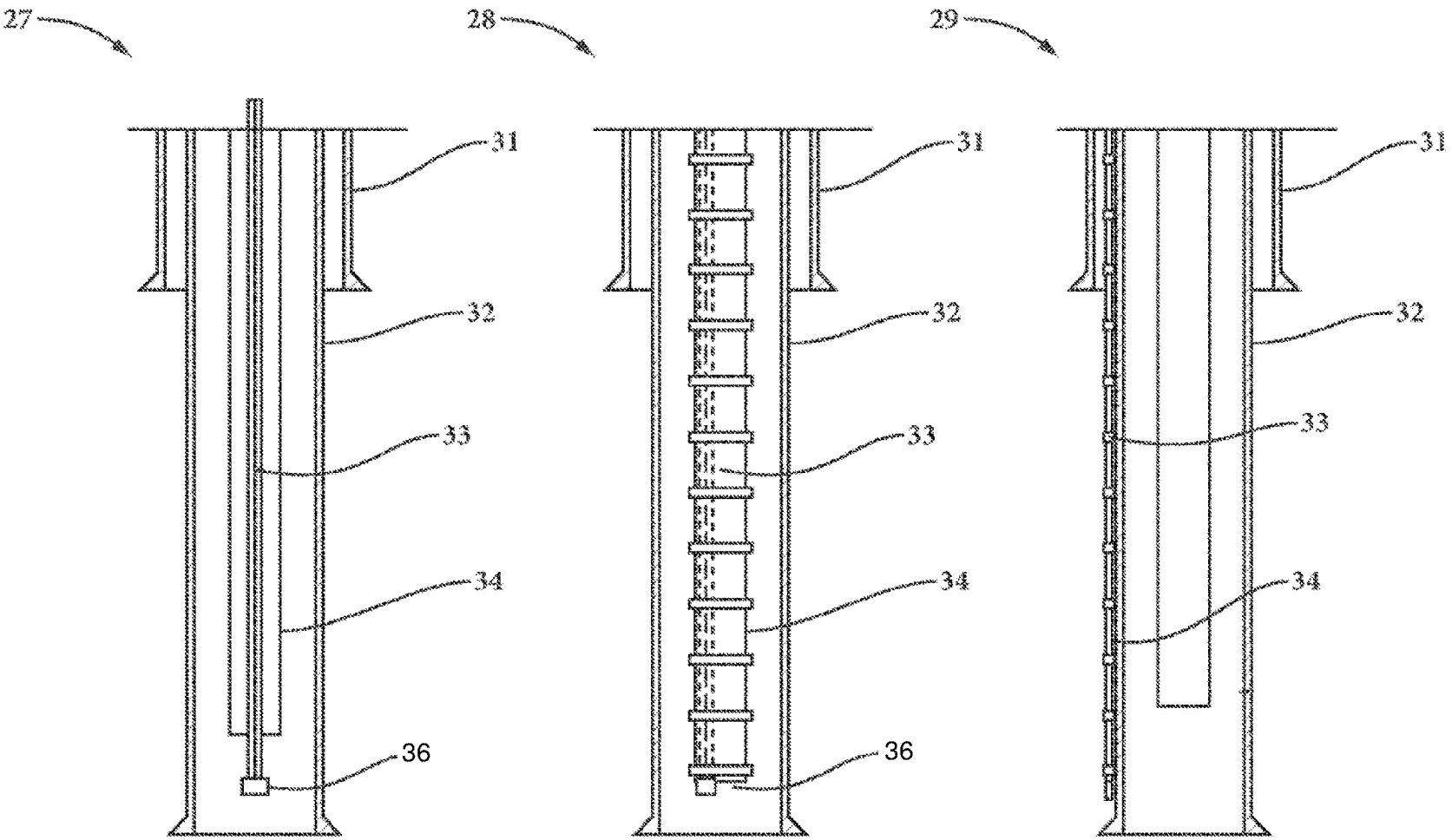
FIG 5
AMENDED

SYSTEMS AND METHODS FOR SPREAD SPECTRUM DISTRIBUTED ACOUSTIC SENSOR MONITORING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[Not applicable.] *This Reissue Application is a reissue of U.S. patent application Ser. No. 14/903,503, filed Jan. 7, 2016, which issued on Aug. 15, 2017 as U.S. Pat. No. 9,733,120.*

BACKGROUND

Fiber-optic sensors are increasingly being used as devices for sensing some quantity, typically temperature or mechanical strain, but sometimes also displacements, vibrations, pressure, acceleration, rotations, or concentrations of chemical species. The general principle of such devices is that light from a laser is sent through an optical fiber and there experiences subtle changes of its parameters either in the fiber itself or in one or several point-location sensing fiber Bragg gratings and then reaches a detector arrangement which measures these changes.

In particular a growing application field is the use of fiber optic sensing system for acoustic sensing, especially Distributed Acoustic Sensing (DAS). DAS optical fibers can be deployed into almost any region of interest and used to monitor for occurrences that generate acoustic perturbations. DAS is quickly becoming recognized as a powerful tool for remote sensing in oil and gas operations. The list of existing and potential applications in remote sensing for this new technology continues to grow and includes not only downhole or subsurface applications but other applications in which acoustic perturbations are of interest, such as subsea umbilical's and risers, and in the security field for perimeter security. Basically any structure can be monitored for acoustic perturbations in this way. Traditionally, DAS applications in the subsurface environment use pulsed electromagnetic waves to interrogate a fiber optic cable for sensing acoustic and vibration phenomena in an oil well, or reservoir. This type of sensor is sometimes referred to as a time-domain coherent optical reflectometer and utilizes a technique called time division multiplexing. In summary, a short electromagnetic coherent pulse (usually in the infrared) is injected into one end of a fiber optic. Pulses are back reflected or backscattered via Rayleigh scattering along a continuum of virtual reflectors in the fiber and these pulses are analyzed using interferometric techniques. A phase of the returned light is measured that is related to the local stretch in the fiber optic during its exposure to an acoustic pressure wave. The optical phase ideally will vary linearly with the acoustic pressure wave. Once a light pulse is injected, a period of time should be surpassed before injecting another pulse of light. This amount of time is twice the transit time of light from the injection location to the end of the fiber. This is done to ensure there is no light in the fiber when another pulse of light is injected. The pulse repetition frequency of the DAS is the reciprocal of the wait time between light injections. Half of the pulse repetition frequency is the well-known Nyquist frequency, which is the maximum acoustic bandwidth available for monitoring.

As the business intensity grows in the worldwide campaign to find and produce more oil there is increasing need to better monitor subsurface oil field operations using more sophisticated acoustic monitoring. In particular there are increasingly applications in which there is a need for detecting much higher frequency and higher bandwidth acoustic signals than that available with time division multiplexing alone. Examples include an increasing interest in listening for sand flow, high bandwidth telemetry, listening for proppant in hydraulic fracturing operations, measuring fluid flow by acoustic signatures (particularly with active ultrasonic flow monitoring systems), monitoring flow regimes, listening for wellbore leaks (often high frequency), listening for cavitation in flow, listening for plug leaks or inter-zone leaks, monitoring vortex shedding, and wireline sonic logging. These applications require a sensitive listening device with an increased audio bandwidth and an improved signal-to-noise ratio.

The technical approach to be described in this application does not rely on the pulsed laser time division multiplexing described above.

BRIEF DESCRIPTION OF THE DRAWINGS

FIG. 5 illustrates some options of wellbore monitoring of an oil well.

DETAILED DESCRIPTION

Figure 1:
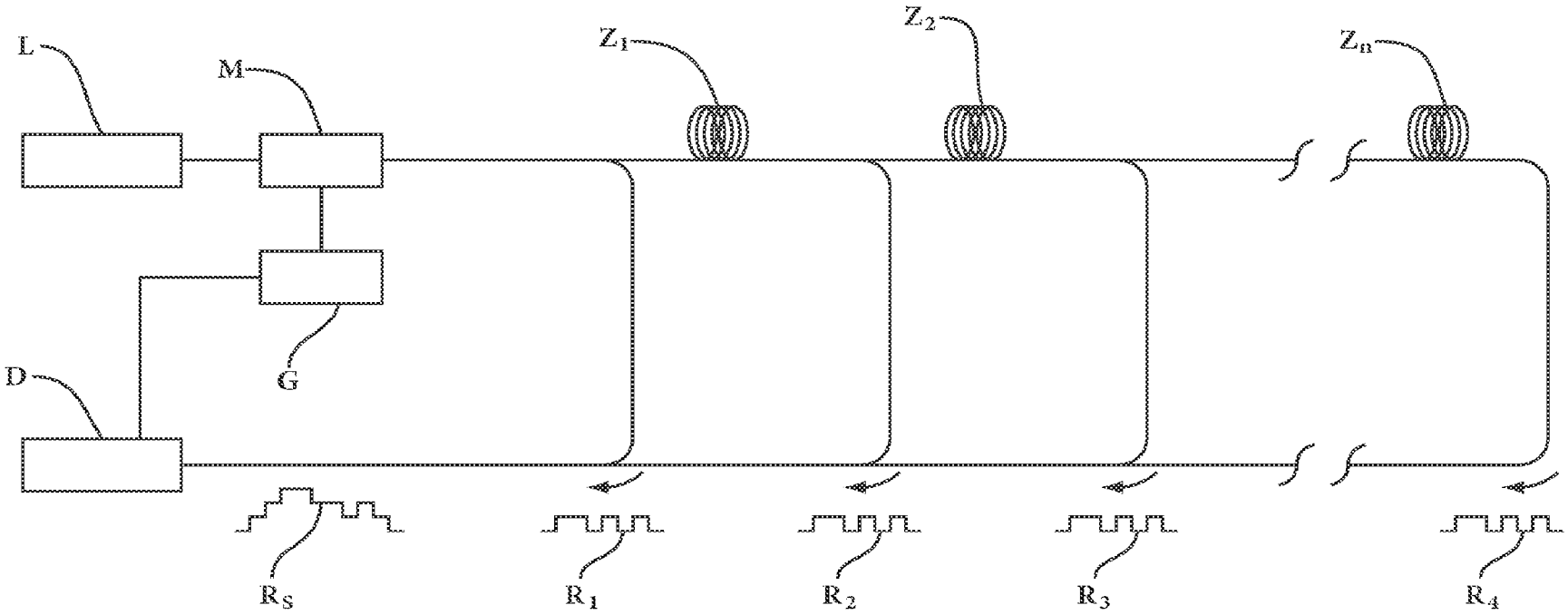
FIG. 1 is a symbolic illustration of the way return signals from spread spectrum system are summations of many time delayed binary modulations.

In the following detailed description, reference is made that illustrate embodiments of the present disclosure. These embodiments are described in sufficient detail to enable a person of ordinary skill in the art to practice these embodiments without undue experimentation. It should be understood, however, that the embodiments and examples described herein are given by way of illustration only, and not by way of limitation. Various substitutions, modifications, additions, and rearrangements may be made that remain potential applications of the disclosed techniques. Therefore, the description that follows is not to be taken in a limited sense, and the scope of the disclosure is defined only by the appended claims.

Traditional distributed acoustic sensing is analogous in some ways to radar techniques used in traditional pulse-echo so ranging techniques. A short electromagnetic coherent pulse (usually in the infrared) is injected into one end of a fiber optic. Pulses are back reflected via Rayleigh scattering along a continuum of virtual reflectors in the fiber and these pulses are analyzed using interferometric techniques. A phase is measured that is related to the local stretch in the fiber optic during its exposure to an acoustic pressure wave.

The phase ideally will vary linearly with the acoustic pressure wave. In a sense, a conventional distributed acoustic sensor acts as a radar with a virtual continuum of reflections from Rayleigh scattering along the fiber, similar to radar measurements of extended bodies such as rain clouds.

An alternative to utilizing traditional pulsed ranging measurements is spread spectrum-ranging methods. Some spread spectrum modulation techniques make use of multiplexing and de-multiplexing methods commonly grouped into a technology known as code division multiplexing. This method consists of mixing or modulating a coherent (near) single frequency signal with a pseudo random signal code that has a broad spectrum relative to the signal being sensed. We will describe solutions employing bipolar codes having +1 and −1 values. The sequence does not allow zeroes since that would result in a signal chopped in time. The receiver demodulates or recovers the original signal with a binary code that is uniquely paired (or nearly so) with the original binary code. Each code sequence modulates the coherent signal for short period of time and is generally immediately followed by another code sequence modulation, followed by another, and so on, with requirements known to those skilled in the art.

Each of the reflected signals occupies a unique time-delay slot or bin. And by delaying and multiplying the code sequence and multiplying it by the received signal, we can recover the frequency-modulated signal. A master or carrier wave is modulated by a single code sequence and delayed by the appropriate time interval specific to a particular signal. All such signals are combined by the action of the fiber optic and the transmitted signal consists of a continuous wave pulse that is multiplied by a single coding sequence and transmitted as a composite optical signal to a receiver where these are collected and photo detected. By filtering the photo detected composite optical signal with the master or reference carrier wave, each individual optical signal is sorted or de-multiplexed into separate electronic signal channels.

The phase of the de-multiplexed signal can then be extracted by a frequency modulation (FM) demodulation scheme.

In conventional time-domain reflectometry using fiber optic cables or other mediums such as glass, air, water, etc. over lengths typical of wellbores, the maximum detectable acoustic bandwidth is bandwidth limited. For example, a 10 km fiber optic cable has a maximum acoustic bandwidth of 5 kHz. Time-domain reflectometry methods do not sample the optical medium fast enough to detect tens or hundreds of kilohertz bandwidth variations in the medium. There is a considerable range of events that occur in a well that produce acoustic perturbations. Multiple fluids and phases (gas bubbles, solids, and some liquid mixtures) may produce recognizable acoustic signatures. The extension of reflectometry into much higher frequencies by the use of the spread spectrum technique of this disclosure can open acoustic monitoring into a realm of new application space—to include an increasing interest in listening for sand flow, high bandwidth telemetry, listening for proppant in hydraulic fracturing operations, measuring fluid flow by acoustic signatures (particularly with active ultrasonic flow monitoring systems), monitoring flow regimes, listening for wellbore leaks (often high frequency), listening for cavitation in flow, listening for plug leaks or inter-zone leaks, monitoring vortex shedding, and wireline sonic logging.

These applications require a sensitive listening device with an increased audio bandwidth and an improved signal-to-noise ratio. Both are characteristics of spread spectrum techniques. It is anticipated that all of these applications can be addressed with the system and method described herein.

The approach also relates to fiber optic sensors and optical sensors generally. A fiber optic sensor array is typically time-domain multiplexed by the time-of-transversal of an interrogation light wave to each sensor and back to a common optical collection and detection point In the technology to be described the continuous wave output of a long coherence length phase-stable infrared laser is modulated with pseudo-random binary code sequences. This is the spread spectrum modulation of a laser using special binary codes. These binary code sequences consist however of ones and negative ones instead of ones and zeros.

The construction or selection of a suitable binary code sequence, or sets of sequences, is not trivial. To guarantee efficient spread-spectrum communications, the pseudorandom number sequences must respect certain rules, such as length, auto-correlation, cross-correlation, orthogonality, correlation sidelobe behavior, and bits balancing. The more popular pseudorandom number sequences have names such as Barker, M-Sequence, Gold, Hadamard-Walsh, etc.

Good code sequences for this application have a high, narrow auto-correlation peak, when exactly lined up, which minimizes false synchronization. Auto-correlation is the same as cross-correlation, except with auto-correlation the code is compared against itself, with a relative shift of one chip at a time. With cross-correlation the code sequence is compared against another code sequence with a relative shift of one chip at a time.

Figure 6:
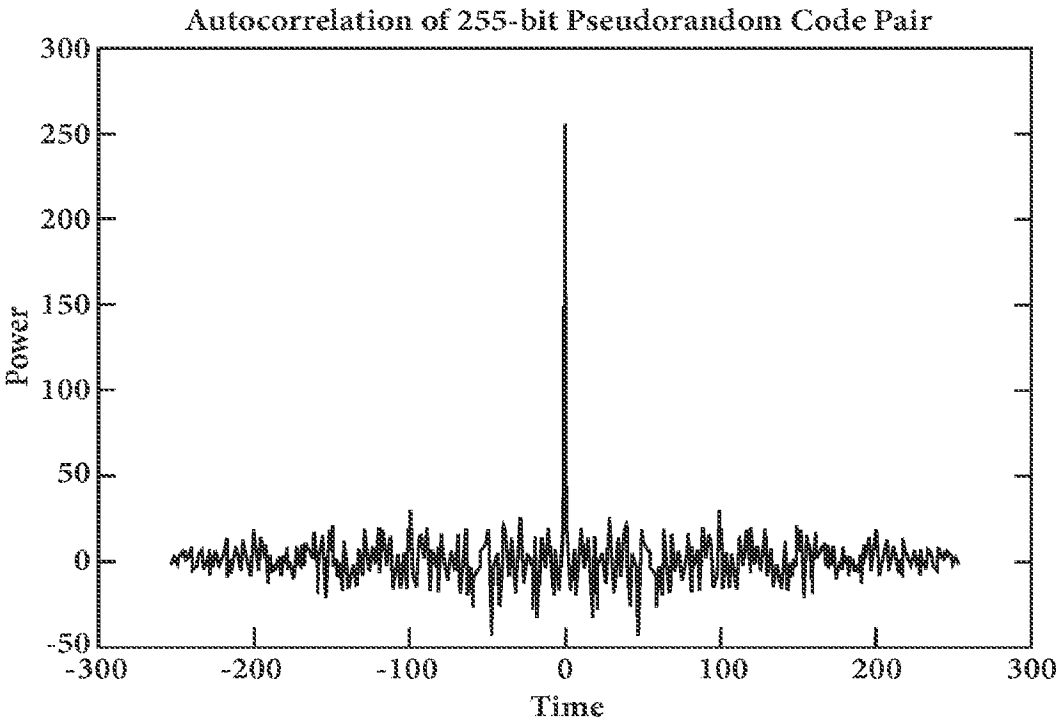
FIG. 6 illustrates an auto-correlation plot of a spread spectrum code.

In the approach to be described in this disclosure, the focus is on auto-correlation. The only property of the code currently being used is the fact that, when the code is multiplied by itself, the result is one when the two versions of the code are time-aligned and a small noise-like signal when they are not time-aligned. The auto-correlation function of the code informs us of how much time-delay we can impose on the code before the product becomes noise-like. The more impulsive the auto-correlation signal, the smaller the delay we need to have a noise-like signal. An example of the power of autocorrelation in providing strong signal-to-noise ratios is shown in FIG. 6.

Pseudo-random spreading codes have a fixed length. After a fixed number of chips (the code length) they repeat themselves exactly. Codes may be formed using a shift register with feedback taps. For example a common useful series of codes (maximal length codes) of 127 chips long may be formed using a 7-bit shift register.

Furthermore, the correlation function of a signal with itself is negligible except when the function overlap is perfect or synchronized. The correlation function of two different signals of a binary code set result in a negligible output. The presence of other coded signals superimposed on particular coded signal does not appreciably or noticeably affect the detection of said code sequence.

Range determination along the fiber is made possible via the correlation properties of the spread spectrum encoding which uniquely encodes the time-of-flight along the length of the fiber. Note that the response at the receive end of the fiber will be the summation of Rayleigh backscattered signal from the continuum of virtual mirrors along the fiber. Each time-shifted signal can be treated independently since the signal from each virtual mirror will not correlate with each other. This is a key property and advantage of spread spectrum methods. Advantages of spread spectrum include resistance to interference, particularly from signals with different spread spectrum coded signals.

This is illustrated symbolically in FIG. 1, which is neither prior art nor the system of this disclosure but a symbolic representation of a return signal $R_S$ that is the summation of multiple delayed output returned optical signals $R_1$, $R_2$, $R_3$, $R_4$ returned from various regions $Z_1$, $Z_2$, . . . $Z_n$ along an extended optical fiber. Modulator M based on a pseudorandom code provided by code generator G modulates a light source L. Each backscattered signal $R_1$, $R_2$, $R_3$, $R_4$, comes from a different position, but arrives back at a detection system D as a net sum binary modulation that can be deconstructed using heterodyne or homodyne demodulation, decoding, and FM demodulation.

There are numerous binary sequences that have properties that are advantageous for particular cases. Some codes have so-called orthogonality properties and some have features related to auto-correlation and cross-correlation. These codes are sometimes referred to as pseudorandom noise (PRN) codes. Sometimes these are simply referred to as PN-codes. Pseudorandom noise code sequences are deterministically generated but have properties similar to random sequences generated by sampling a white noise process. Some commonly used PN codes include, but are not limited to, are 1) Gold
2) Kasami
3) Golay
4) Hadamard-Walsh
5) M-Sequences (binary maximal-length linear feedback shift register sequences)

Overview—Spread Spectrum

To describe and clarify the techniques of the use of spread spectrum codes in this application and to further define the terminology the following mathematical description is presented. Spread spectrum begins by the insertion of a probe signal:

$$E_i(t)=c(t)\cos(\omega_s t),$$

where c(t) is a spread-spectrum code signal, such that $\int c(t)c(t+\tau)dt=\delta(\tau)$, and $\omega_s$ is the carrier frequency. This results in the reception of the signal:

$$E_b(t)=\int_0^{\hat{Z}} r(z)\mu_A c(t-2c_L^{-1}\hat{z}(t,z))E_{ss}\cos(\omega_s(t-2c_L^{-1}\hat{Z}$$

where $c_L$ is the speed of light, $E_{ss}$ and $\mu_A$ are constants, r(z) is the distributed reflection along the fiber, and $$\left[\hat{z}(t, z) = z + \mu_L \int_0^z p(t, x)dx\right]$$

$$\hat{z}(t, z) = z + \mu_L \int_0^z p(t, z)dz$$

with p(t,z) being the pressure at position z and time t.

Then upon heterodyne (or homodyne) demodulation to a baseband signal (but with the signal still spread):

$$b(t) = [E_b(t)\cos((\omega_s + \Delta_\omega)t)] * h_{LP}(t) \approx \int_0^{\hat{Z}} r(z)\mu_A c(t - 2c_L^{-1}\hat{z}(t, z))E_{ss}\cos(\Delta_\omega t - 2\omega_s c_L^{-1}\hat{z}(t, z))dz,$$

where $h_{LP}(t)$ is a low-pass filter that removes the undesired spectral components around $2\omega_s$. In the case of homodyne demodulation $\Delta_\omega=0$.

Then the demodulated baseband signal can be decoded by:

$$\bar{b}(t, z_i) = [c(t - 2c_L^{-1}z_i)b(t)] * h_{PB}(t) = \left[\int_0^{\hat{Z}} r(z)\mu_A c(t - 2c_L^{-1}z_i)c(t - 2c_L^{-1}\hat{z}(t, z))E_{ss}\cos(\Delta_\omega t - 2\omega_s c_L^{-1}\hat{z}(t, z))dz\right] * h_{PB}(t) \approx r(z_i)\mu_A E_{ss}\cos(\Delta_\omega t - 2\omega_s c_L^{-1}\hat{z}(t, z_i)).$$

Where $h_{PB}(t)$ is a band pass filter for heterodyne demodulation or a low-pass filter for homodyne demodulation.

More information regarding decoding is provided in the next section.

Decoding Analysis

Incorporating the information from the pass-band filter $h_{PB}(t)$ into the de-spreader:

$$\bar{b}(t, z_i) = [c(t - 2c_L^{-1}z_i)b(t)] * h_{PB}(t) = \left[\int_0^{\hat{Z}} r(z)\mu_A c(t - 2c_L^{-1}z_i)c(t - 2c_L^{-1}\hat{z}(t, z))E_{ss}\cos(\Delta_\omega t - 2\omega_s c_L^{-1}\hat{z}(t, z))dz\right] *$$

$$h_{PB}(t) = \int_0^\infty \int_0^{\hat{Z}} h_{PB}(t - \tau)r(z)\mu_A c(\tau - 2c_L^{-1}z_i)c(\tau - 2c_L^{-1}\hat{z}(\tau, z))$$

$$E_{ss}\cos(\Delta_\omega \tau - 2\omega_s c_L^{-1}\hat{z}(\tau, z))dz\,d\tau = \int_0^{\hat{Z}} E_{ss}r(z)\left[\int_0^\infty h_{PB}(t - \tau)\right.$$

$$\left.\mu_A c(\tau - 2c_L^{-1}z_i)c(\tau - 2c_L^{-1}\hat{z}(\tau, z))\cos(\Delta_\omega \tau - 2\omega_s c_L^{-1}\hat{z}(\tau, z))d\tau\right]dz$$

If we now assume that:

$$c(\tau - 2c_L^{-1}\hat{z}(\tau, z)) = c\left(\tau - 2c_L^{-1}\left(z + \mu_L \int_0^z p(t, x)dx\right)\right) \approx c(\tau - 2c_L^{-1}z),$$

that is, that the time delay variation caused by the acoustic pressure is negligible when compared to the time delay caused by the time of flight of the optic wave; it is possible to write:

$$\bar{b}(t, z_i) \approx \int_0^\infty E_{ss}r(z)\left[\int_0^\infty h_{PB}(t - \tau)\mu_A c(\tau - 2c_L^{-1}z_i)c(\tau - 2c_L^{-1}z)\cos(\Delta_\omega \tau - 2\omega_s c_L^{-1}\hat{z}(\tau, z))d\tau\right]dz.$$

It will be considered that the code c(t) has bandwidth $\sigma_c$, and also has the following property:

$$c(t)c(t + \delta) \approx \begin{cases} 1, & \text{if } |\delta| \le \epsilon \\ d(t), & \text{if } |\delta| > \epsilon \end{cases}$$

where function d(t) is the result of spreading the code twice, and has a bandwidth of $2\sigma_c$. Hence, the integration region in the z variable can be decomposed into two disjoint sets:

$$\mathcal{R}_1=\{z|z\le z_i+|c_L\epsilon^{-1}|\}$$

$$\mathcal{R}_2=\{z|z>z_i+|c_L\epsilon^{-1}|\}.$$

Thus the received signal can be written as:

$$\bar{b}(t, z_i) \approx \int_{z_1 \in \mathcal{R}_1} E_{ss} r(z_1) \left[ \int_0^{\infty} h_{PB}(t-\tau) \mu_A \cos\left(\Delta_\omega \tau - 2\omega_s c_L^{-1} \hat{z}(\tau, z_1)\right) d\tau \right] dz_1$$

If the FM signal bandwidth is $\sigma_{FM}$, then most of the information of region in $\mathcal{R}_2$ is spread by the function d(t), and has bandwidth $2(\sigma_c+\sigma_{FM})$ and is centered around frequency $\Delta_\omega$, and most of the information of region in $\mathcal{R}_1$ is concentrated in frequency, has a bandwidth of $\sigma_{FM}$, and is centered around frequency $\Delta_\omega$.

With that information, it is possible to specify the filter $h_{PB}(t)$ with center frequency $\Delta_\omega$ and passband of $\sigma_{FM}$ that removes most of the information from the region $\mathcal{R}_2$ while leaving the information from $\mathcal{R}_1$ unaltered.

The decoded signal, then, can be written as:

$$\bar{b}(t,z_i) \approx \omega_{z_i - c_L \epsilon^{-1}}^{z_i + c_L \epsilon^{-1}} E_{ss} r(\mu_A \cos(\Delta_\omega \tau 2\omega s c_L^{-1} \hat{z}(\tau, z)) dz + v(t,z),$$

where v(t,z) is a nuisance signal. It is also possible to note:

The larger the bandwidth of $\sigma_c$ relative to $\sigma_{FM}$, the easier it is to remove the interference from other spatial regions of the fiber.

The smaller the value of $\epsilon$, the better the tuning of the spatial information, thus allowing more spatial points to be sampled.

On the other hand, the value of E cannot be so small as to make the approximation that the time delay variation caused by the acoustic pressure is negligible compared to the time delay caused by the time of flight of the optic wave invalid.

The higher the beat frequency $\Delta_\omega$, the more selective the filter $h_{PB}$ must be.

The center frequency should be high enough so that it is possible to retrieve the acoustic pressure signal.

Acoustic Signal and FM Signal Bandwidth

Ideally, the decoded FM signal captured at position $z_i$ is:

$$\bar{b}^{+}(t, z_i) = r(z_i) E_s s \mu_A \cos\left(\Delta_\omega t - 2\omega_s c_L^{-1} z_i - 2\omega_s c_L^{-1} \mu_L \int_0^{z_i} p(t, x) dx\right).$$

Carson's rule states that for a signal of the form:

$$s_{FM}(t) = A_c \cos(\omega_c t + f_\Delta \Psi(t)),$$

and its bandwidth is:

$$\sigma_{FM} = 2(f_\Delta + \sigma_A),$$

where $\sigma_A$ is the bandwidth of the modulating signal.

Adapting the Carson's rule for the decoded signal, one obtains:

$$\sigma_{FM} \approx 2\left(\frac{2\omega_s \mu_L}{c_L} + \sigma_A\right) = 2(\sigma_\Delta + \sigma_A),$$

where this approximate $\sigma_{FM}$ usually covers 98% of the energy of the FM signal. It should also be noted that $\sigma_A$ is actually the bandwidth of the derivative of $p(t, z_i)$. In practice, since there are an infinite number of p(t,z) influencing the FM signal, the worst-case (largest possible value of $\sigma_A$) should be selected. Alternatively, a bandwidth for the acoustic pressure can be arbitrarily chosen and then the assumed FM signal bandwidth can be determined.

With this background and term definition we are now in a position to propose a code design.

Code Design

We have found that for the applications of this disclosure Maximal Length Sequences (M-Sequences) and the use of auto-correlation provide excellent code candidates. In particular, two parameters are of interest for the spread spectrum sensing using fiber optics: the $\epsilon$ of the sequence and its bandwidth. $\epsilon$ (epsilon) is the smallest delay to the signal for which the sequence can be recovered. Any delay larger than epsilon, produces a noise-like sequence.

M-Sequences are bipolar sequences that can be generated through the use of a feedback-shift register (FSR). For the sake of the following discussion, it will be considered that $c(t) \in \{-1,1\}$ and that it is periodic with period equal $T_b$, also the minimum period that the code stays at a certain value is $T_c$.

The following properties are true for an m-sequence.

Its auto-correlation is $$R_c(\tau) = \begin{cases} 1 - \frac{N+1}{NT_c}|\tau|, & |\tau| \le T_c \\ -\frac{1}{N}, & T_c < |\tau| \le T_b \end{cases},$$

where $T_b = NT_c$.

The product of two time-aligned codes is $c^2(t)=1$.

Its power spectral density is $$S_c(f) = \frac{1}{N^2}\delta(f) + \frac{1+N}{N^2} \sum_{n=-\infty}^{n=\infty} \mathrm{sinc}^2\left(\frac{n}{N}\right) \delta\left(f - \frac{n}{NT_c}\right),$$

and the spectrum is discrete-valued and has an envelope that follows that of a $\mathrm{sinc}^2(\bullet)$ function. Using this information it is possible to approximate the signal bandwidth. Hence, the bandwidth of $\sigma_c$ can be approximated as 2/Tc.

Code Requirements

Using the properties just defined in the previous section, the following specifications can be defined for a coding sequence.

The symbol period $T_c$ is related to the autocorrelation properties of the sequence. Also, it can be seen that the shorter the period the more different two time shifted codes become. Hence, the parameter $\epsilon$ is directly proportional to $T_c$:

$$\epsilon \propto T_c,$$

The smaller the $T_c$, the better is the ability of the code to pick out the signal from a desired position.

The possible spatial sampling $\Delta_z$ of the z axis is also governed by the choice of $T_c$. A conservative separation between positions equal to $$\Delta_z = \frac{c_L}{\epsilon} = \frac{c_L}{T_c}.$$

Thus, the smaller the period of the code the greater the number of positions that can be sampled.

The symbol period is also related to the code bandwidth. In order to yield a good separation of signals from neighboring regions, the code bandwidth should be greater than the bandwidth of the FM signal:

$$\sigma_c = 2/Tc >> 2(\sigma_\Delta + \sigma_A),$$

where $\sigma_\Delta$ is the spread in frequency introduced by frequency modulation and $\sigma_A$ is the acoustic signal bandwidth. so that, $$\frac{6\pi}{(\sigma_\Delta + \sigma_A)} \gg (NT_c).$$

Since the code is periodic, its period $T_b$ should be greater than that of the time it takes for the light to transverse the whole fiber optic cable and arrive back at the receiver. Mathematically $$T_b = NT_c > \frac{2L}{c_L},$$

where L is the length of the fiber optic.

Combining the equations above, one has $$\frac{6\pi}{(\sigma_\Delta + \sigma_A)} \gg NT_c > \frac{2L}{c_L},$$

which gives a loose upper bound and a more tight lower bound for the requirement for the code length. Considering these bounds, a good strategy would be to use a code with length close to (but not equal to)

$$\frac{2L}{c_L}.$$

The following steps would then be employed to specify the system:

1. Specify the fiber optic cable length L, the desired spatial sampling $\Delta_z$, and acoustic signal bandwidth $\sigma_A$.
2. Choose $T_b$ so that $$T_b = \frac{2L}{c_L} + \rho,$$

where ρ is small when compared to $$\frac{2L}{c_L};$$

3. Choose N so that $NT_c = T_b$ and $T_c$ so that $$\Delta_z = \frac{c_L}{\epsilon} = \frac{c_L}{T_c}.$$

Figure 2:
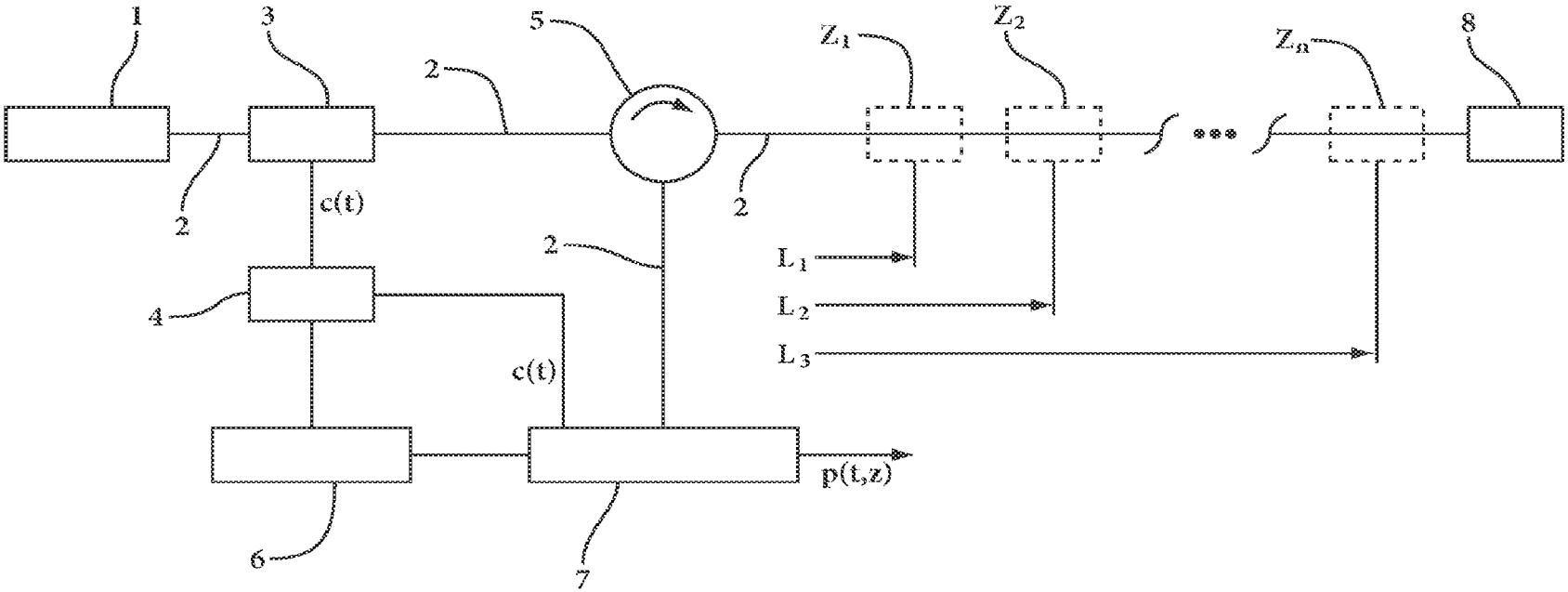
FIG. 2 illustrates a block diagram of a distributed acoustic sensing system in accordance with this description.

Turning now to FIG. 2, a system for monitoring region of interest for occurrences that generate acoustic perturbations is described. A fiber optic waveguide 2 is positioned into a region of interest, which may be an oil or gas wellbore, oil or gas reservoir, or an extended pipeline. Some possible deployments will be illustrated in a later figure. A light source 1 is used to generate a continuous primary coherent signal of a pre-determined wavelength that is fed to the fiber optic waveguide. A binary code sequence generator 4, coupled to a master clock 6 supplies an electronic code c(t) to an optical modulator 3 that receives the primary coherent light signal and modulates it based on the input from the binary code sequence generator. The now modulated light signal from modulator 3 then enters an optical circulator/coupler 5 that receives the modulated light signal and passes it into the optical fiber span positioned in the region of interest. Positions $Z_1, Z_2, \ldots Z_n$ along the deployed optical fiber span represent locations at lengths $L_1, L_2, \ldots L_n$ at which the modulated light signal interacts with the optical fiber and returns backscattered Rayleigh signals. The numeral 8 represent the terminal end of the deployed optical waveguide. The backscattered Rayleigh signals are directed by the optical circulator/coupler 5 into a detector 7 that performs functions of heterodyne demodulation, decoding, and FM demodulation. Detector 7 also has photo detectors for detecting and measuring the light signals and a processor for directing all of the functions of demodulation and decoding necessary to produce measured the desired acoustic pressure signals p(t,z) along the length of the deployed optical fiber span.

Figure 3:
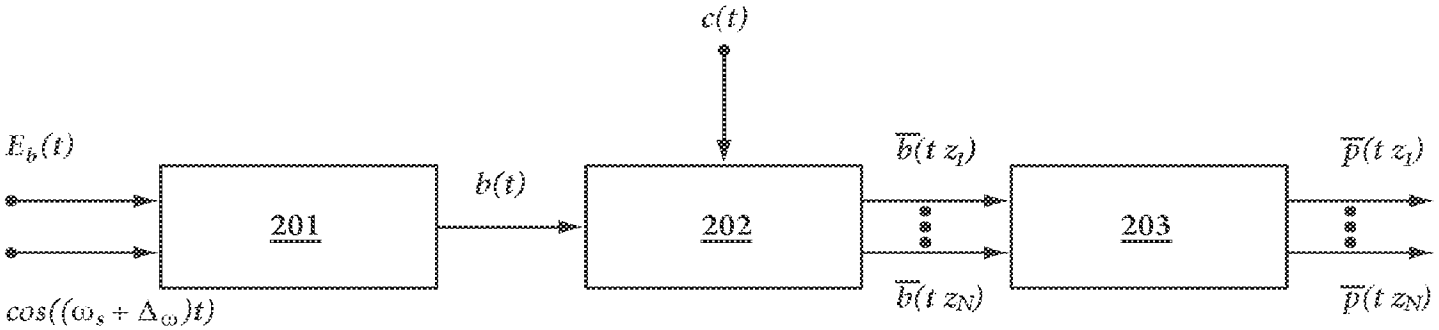
FIG. 3 illustrates a more detailed view of the details within element 7 of FIG. 2.

A more detailed depiction of the detector system 7, to explain the separate functions of heterodyne or homodyne demodulation, decoding, and FM demodulation is shown in FIG. 3. In section 201 the optical signal is heterodyne demodulated by combining the optical signal $E_b(t)$ with another optical signal $\cos((\omega_s+\Delta_\omega)\ t$ that is shifted in frequency by $\omega_s+\Delta_\omega$ relative to the received signal. For homodyne demodulation $\Delta_\omega=0$. The output of demodulator 201, now an electronic signal, is submitted to decoder 202, which extracts the information of the positions $Z_1, Z_2, \ldots, Z_n$ of the fiber which are being sensed. The phase of each of the signals are then extracted by the FM Demodulator and the acoustic pressure signal $p(t,z_1) \ldots p(t,z_n)$ associated with each position along the fiber is obtained. Not shown in the elements of the detector system would be photo detectors and a processor for controlling all of the functions and computations of the detector system and providing the output of acoustic pressure signals.

Figure 4:
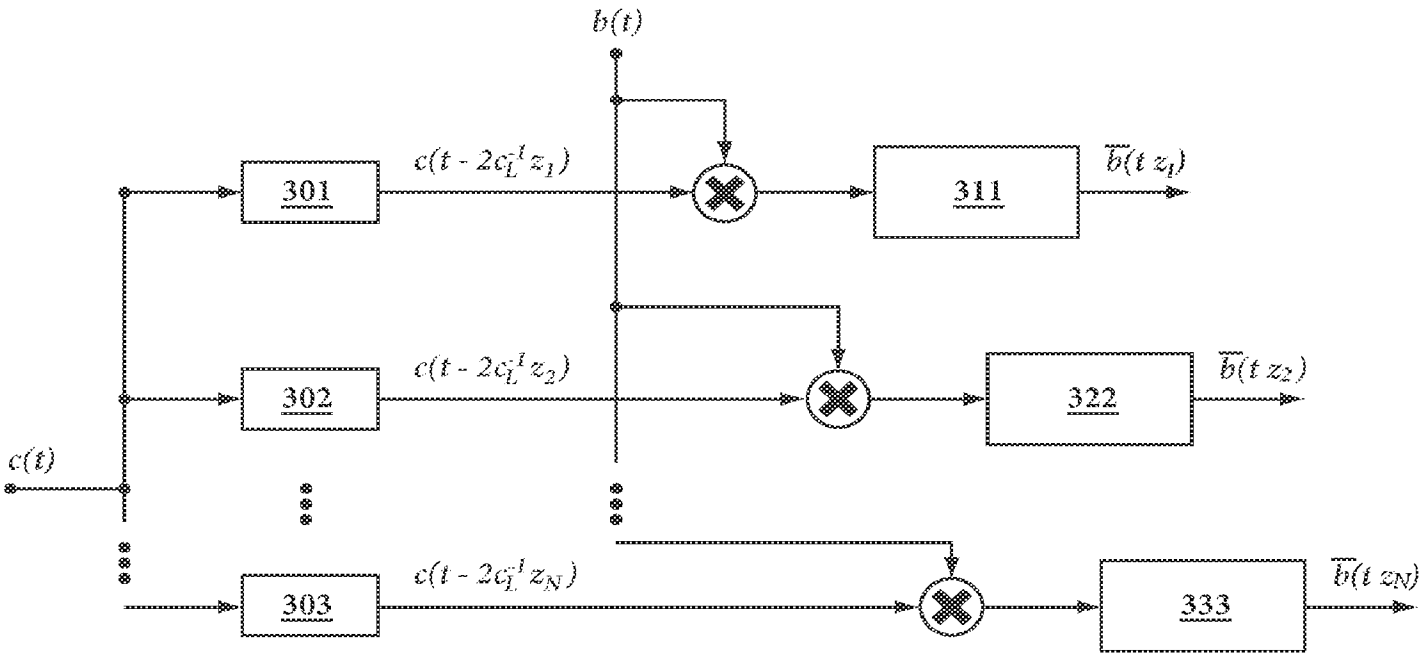
FIG. 4 illustrates a more detailed view of the details within element 202 of FIG. 3.

FIG. 4 exhibits more details regarding decoder 202 of FIG. 3. The decoder provides circuitry for separating the electronic signal b(t) from the heterodyne demodulator into separate branches representing the positions $Z_1, Z_2, \ldots, Z_n$ along the sensing fiber optic. The binary coding sequence c(t) is also split into several signals, each signal being time delayed with a delay proportional to the time it takes for the code to arrive at a defined position of the fiber. The circuitry for providing this functionality could be provided either analogically or digitally. The electronic signal and the delayed coding sequences are then multiplied in time and band-pass filtered (low-pass filtered in the case of homodyne demodulation) to obtain a signal that only contains the information of a certain position of the optical fiber.

Some possible configurations for deployment of distributed sensing systems in and around a wellbore are shown in FIG. 5, as 27, 28, and 29. These configurations are examples and not meant to be exhaustive. Configuration 27 is a fairly typical retrievable wireline in which a fiber optic cable 33 is deployed within metal tubing 34 and down to a bottom hole gauge or termination 36. The metal tubing 34 is surrounded by production casing 32, which is surrounded by a surface casing 31 near the surface. Configuration 28 represents a permanent tubing installation in which a fiber optic cable 33 is attached to metal tubing 34. And configuration 29 represents a casing attachment in which the fiber optic cable 33 is attached outside the production casing 32. As discussed earlier there are other possible configurations (not shown) when using distributed sensing systems in applications such as perimeter security systems, monitoring of subsea umbilical's, risers, or pipelines.

Figure 7:
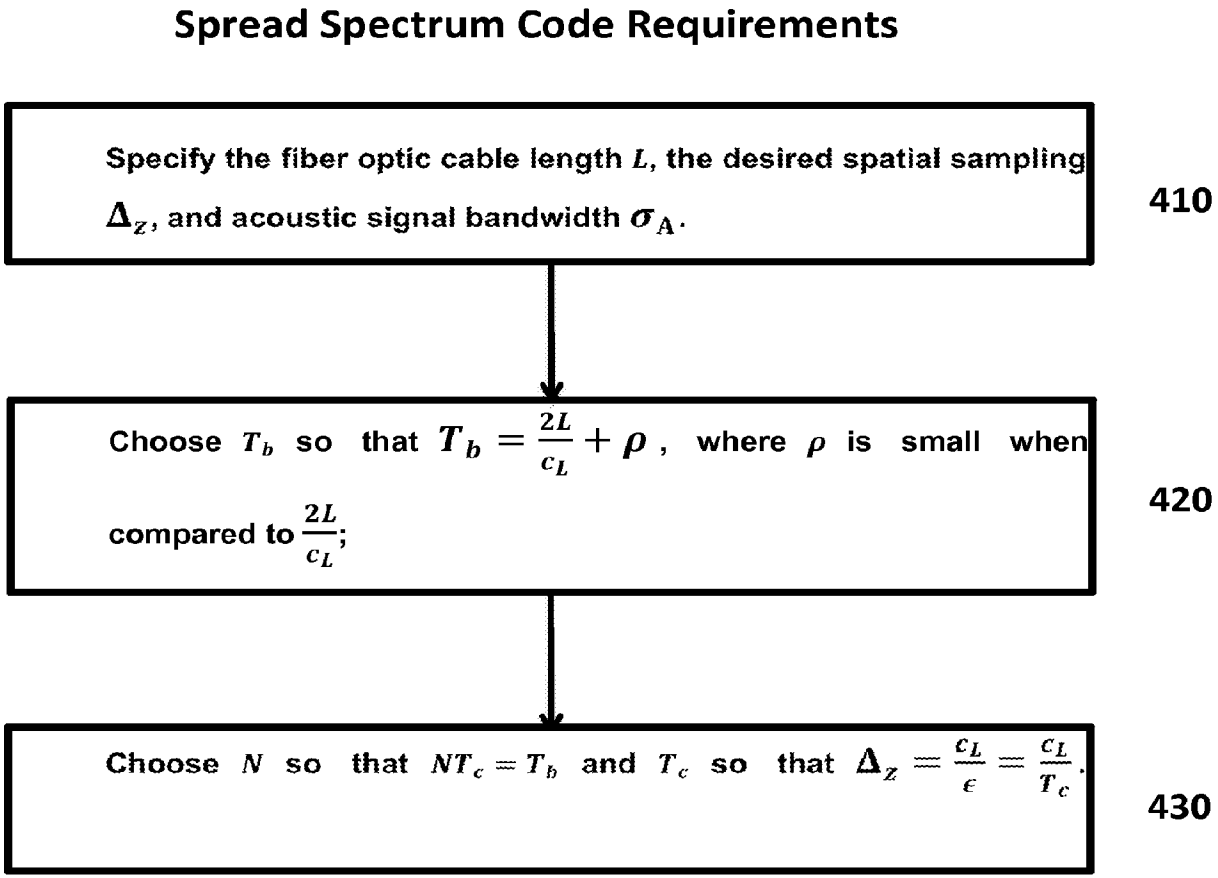
FIG. 7—illustrates a flow chart representation of the method steps used in an embodiment of this description.

FIG. 7 spells out the preferred code requirements for the Maximal Length Sequences (M-Sequences) proposed in this disclosure along with the use of auto-correlation. In step 410 the practitioner specifies the fiber optic length, the desired spatial sampling, and the acoustic bandwidth. Then in step 420 Tb is chosen so that it is very close to $$T_b = \frac{2L}{c_L}.$$

Then in step 430 N is chosen so that $NT_c=T_b$ and $T_c$ so that $$\Delta_z = \frac{c_L}{\epsilon} = \frac{c_L}{T_c}.$$

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes. machines, manufactures. means, methods or steps.

The invention claimed is:

1. A system for monitoring regions of interest for occurrences that generate acoustic perturbations, comprising:

a. an optical fiber span positioned into a region of interest;

b. a light source for generating a continuous coherent signal of a pre-determined wavelength into the optical fiber;

c. a pseudo-random binary code sequence generator driven by a master clock;

d. an optical modulator having first and second ports for receiving the primary coherent light signal from the light source and a generated pseudo-random binary codes from the pseudo-random binary code sequence generator to produce a modulated light signal;

e. wherein the pseudo-random binary sequence codes are binary sequences of ones and negative ones;

f. and wherein the pseudo-random binary sequence codes are periodic with a period of $T_b$ and the minimum period that the code stays at a certain value is $T_c$;

g. and wherein the fiber optic cable length L, the desired spatial sampling $\Delta_z$, and the acoustic signal bandwidth $\sigma_A$ are specified in advance for the application; and i. N is chosen so that $NT_c=T_b$;

ii. $T_b$ is chosen so that $$T_b = \frac{2L}{c_L} + \rho,$$

where ρ is small compared to $$\frac{2L}{c_L};$$

and iii. $T_c$ is chosen so that $$\Delta_z = \frac{c_L}{\epsilon} = \frac{C_L}{T_c};$$

h. an optical circulator/coupler to receive the modulated light signal from the optical modulator and pass it into the optical fiber span positioned into the region of interest;

i. a detector system driven by the master clock for de-modulating, correlating, and de-multiplexing returned backscattered Rayleigh signals from the optical fiber span positioned into the region of interest, wherein the detector system has a processor to detect coherent Rayleigh noise generated by the optical fiber span positioned in the region of interest to identify acoustic events in the regions of interest; and j. wherein the returned backscattered Rayleigh signals from the optical fiber span positioned into the region of interest are directed to the detector system by the optical circulator/coupler.

2. The system for monitoring regions of interest for occurrences that generate acoustic perturbations of claim 1, wherein the light source for generating a continuous coherent signal of a pre-determined wavelength is a laser.

3. The system for monitoring regions of interest for occurrences that generate acoustic perturbations of claim 1, wherein the detector system driven by the master clock comprises:

a. a heterodyne or homodyne demodulator;

b. a decoder; and c. an FM demodulator.

4. The system for monitoring regions of interest for occurrences that generate acoustic perturbations of claim 3, wherein the detector system further comprises photo detectors and a processor for controlling all of the functions and computations of the detector system and providing the output of acoustic pressure signals.

5. The system for monitoring regions of interest for occurrences that generate acoustic perturbations of claim 3, wherein the decoder comprises:

a. circuitry for separating the electronic signal from the heterodyne or homodyne demodulator into separate branches representing positions along the sensing fiber optic;

b. circuitry for separating and time delaying the binary coding sequence with a delay proportional to the time it takes for the code to arrive at a defined position of the optical fiber;

c. circuitry for multiplying in time filtering the separated electronic signals from the heterodyne or homodyne demodulator and the corresponding binary coding sequences to obtain signals that contain only the information representing certain positions in the optical fiber; and d. wherein the circuitries can be implemented either analogically or digitally.

6. The system for monitoring regions of interest for occurrences that generate acoustic perturbations of claim 5 wherein the demodulator is a heterodyne demodulator and the circuitry for multiplying in time and filtering the separated electronic signals utilizes band-pass filtering.

7. The system for monitoring regions of interest for occurrences that generate acoustic perturbations of claim 5 wherein the demodulator is a homodyne demodulator and the circuitry for multiplying in time and filtering the separated electronic signals utilizes low-pass filtering.

8. The system for monitoring regions of interest for occurrences that generate acoustic perturbations of claim 5 wherein the region of interest can include a subsurface wellbore, an oil reservoir, or a pipeline.

9. The system for monitoring regions of interest for occurrences that generate acoustic perturbations of claim 5 wherein the region of interest can include structures such as subsea [umbilical's] *umbilicals* or risers.

10. The system for monitoring regions of interest for occurrences that generate acoustic perturbations of claim 5 wherein the region of interest can include perimeters encircling [high security] *high-security* areas.

11. A method for monitoring regions of interest for occurrences that generate acoustic perturbations, comprising:

a. deploying a fiber optic cable into a region of interest;

b. transmitting a continuous wave laser light source through the fiber optic cable;

c. modulating the continuous wave output of the laser light source with pseudo-random binary sequence codes; wherein the pseudo-random binary sequence codes are binary sequences of ones and negative ones;

d. and wherein the pseudo-random binary sequence codes are periodic with a period of $T_b$ and the minimum period that the code stays at a certain value is $T_c$;

e. and wherein the fiber optic cable length L, the desired spatial sampling $\Delta_z$, and the acoustic signal bandwidth $\sigma_A$ are specified in advance for the application; and i. N is chosen so that $NT_c=T_b$;

ii. $T_b$ is chosen so that $$T_b = \frac{2L}{c_L} + \rho,$$

where ρ is small compared to $$\frac{2L}{c_L};$$

and iii. $T_c$ is chosen so that $$\Delta_z = \frac{c_L}{\epsilon} = \frac{C_L}{T_c}.$$

f. detecting backscattered Rayleigh signals from the deployed fiber optic cable; and g. using the detected backscattered Rayleigh signals to identify and measure the acoustic perturbations from locations in the region of interest.

12. The method for monitoring regions of interest for occurrences that generate acoustic perturbations of claim 11 wherein the occurrences are generated by impacts of sand grains.

13. The method for monitoring regions of interest for occurrences that generate acoustic perturbations of claim 11 wherein the occurrences are generated by proppant noise in hydraulic fracturing operations.

14. The method for monitoring regions of interest for occurrences that generate acoustic perturbations of claim 11 wherein the occurrences are generated by [high frequency] *high-frequency* wellbore leaks.

15. The method for monitoring regions of interest for occurrences that generate acoustic perturbations of claim 11 wherein the occurrences are generated by wireline sonic logging.

16. The method for monitoring regions of interest for occurrences that generate acoustic perturbations of claim 11 wherein the occurrences are generated by inter-zone leaks in wellbores.

17. The method for monitoring regions of interest for occurrences that generate acoustic perturbations of claim 11 wherein the occurrences are generated by flow cavitation.

18. The method for monitoring regions of interest for occurrences that generate acoustic perturbations of claim 11 wherein the occurrences are generated by flow vortex shedding.

19. The method for monitoring regions of interest for occurrences that generate acoustic perturbations of claim 11 wherein the occurrences are generated by a particular flow regime.

20. The method for monitoring regions of interest for occurrences that generate acoustic perturbations of claim 11 wherein the occurrences are generated by a particular flow rate.

21. The method for monitoring regions of interest for occurrences that generate acoustic perturbations of claim 11 wherein the occurrences are generated by a particular fluid fraction.

22. The method for monitoring regions of interest for occurrences that generate acoustic perturbations of claim 11 wherein the occurrences are part of an active ultrasonic flow monitoring system.

*23. The method of claim 11 wherein the region of interest includes at least a portion of a perimeter of a high-security area.*

*24. The method of claim 11 wherein the region of interest includes at least one straight portion.*

*25. The method of claim 11 wherein deploying the optical fiber includes deploying the optical fiber to have at least one straight portion.*

*26. A system, comprising:*

*a light source configured to generate a continuous coherent signal of a predetermined wavelength into an optical fiber;*

*a pseudo-random binary code sequence generator configured to be driven by a master clock;*

*an optical modulator having first and second ports configured to receive the primary coherent light signal from the light source and a generated pseudo-random binary codes from the pseudo-random binary code sequence generator to produce a modulated light signal;*

*wherein the pseudo-random binary sequence codes are binary sequences of ones and negative ones;*

*and wherein the pseudo-random binary sequence codes are periodic with a period of $T_b$ and the minimum period that the code stays at a certain value is $T_c$;*

*and wherein an optical-fiber length L, a desired spatial sampling $\Delta_z$, and an acoustic signal bandwidth $\sigma_A$ are specified in advance for the application; and*

*N is chosen so that $NT_c=T_b$;*

$T_b$ is chosen so that $$Tb = \frac{2L}{c_L} + \rho,$$

where ρ is small compared to $$\frac{2L}{c_L};$$

and $T_c$ is chosen so that $$\Delta z = \frac{c_L}{\epsilon} = \frac{C_L}{T_c};$$

an optical circulator/coupler configured to receive the modulated light signal from the optical modulator and to pass it into the optical fiber;

a detector system configured to be driven by the master clock for de-modulating, correlating, and de-multiplexing returned backscattered Rayleigh signals from the optical fiber, wherein the detector system has a processor configured to detect coherent Rayleigh noise generated by the optical fiber to identify acoustic events; and wherein the optical circulator/coupler is configured to direct the returned backscattered Rayleigh signals from the optical fiber to the detector system.

27. A method, comprising:

modulating a continuous-wave light beam with pseudo-random binary sequence codes;

transmitting the modulated continuous-wave light beam through a fiber-optic cable;

wherein the pseudo-random binary sequence codes are periodic with a period of $T_b$ and the minimum period of each code is $T_c$;

and wherein a length of the fiber-optic cable is L, a spatial sampling period along the fiber is $\Delta_z$, and a bandwidth of a sensed acoustic perturbation is $\sigma_A$; and N is chosen so that $NT_c=T_b$;

$T_b$ is chosen so that $$T_b = \frac{2L}{c_L} + \rho,$$

and $T_c$ is chosen so that $$\Delta z = \frac{c_L}{\epsilon} = \frac{C_L}{T_c};$$

detecting backscattered Rayleigh signals from the fiber optic cable; and using the detected backscattered Rayleigh signals to identify and to measure one or more acoustic perturbations from one or more locations along the fiber-optic cable.

* * * * *